(12) United States Patent
Russell et al.

(10) Patent No.: US 7,226,754 B2
(45) Date of Patent: Jun. 5, 2007

(54) KINASE WEE1 FUSION PROTEIN COMPOSITIONS, NUCLEOTIDE SEQUENCES, EXPRESSION SYSTEMS, AND METHODS OF USE

(75) Inventors: Paul Russell, San Diego, CA (US); Michael N. Boddy, Del Mar, CA (US); Beth Furnari, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 339 days.

(21) Appl. No.: 10/375,214

(22) Filed: Feb. 25, 2003

(65) Prior Publication Data

US 2003/0216563 A1    Nov. 20, 2003

Related U.S. Application Data

(62) Division of application No. 09/646,075, filed as application No. PCT/US99/06704 on Mar. 26, 1999, now Pat. No. 6,524,850.

(60) Provisional application No. 60/079,752, filed on Mar. 27, 1998.

(51) Int. Cl.
*C12Q 1/48* (2006.01)
*C12N 9/12* (2006.01)

(52) U.S. Cl. .......................... 435/15; 435/7.1; 435/7.6; 435/194

(58) Field of Classification Search .................. 435/15, 435/7.1, 7.6, 194
See application file for complete search history.

(56) References Cited

OTHER PUBLICATIONS

R. Aligue et al., "Regulation of Schizosaccharomyces pombe Wee1 Tyrosine Kinase", J. Biol. Chem. 272(20):13320-13325. (May 1997).*

Honda, et al. Mouse p87wee1 Kinase is Regulated by M-Phase Specific Phosphorylation. *Chromosome Res.*, 3(5): Aug. 1995. 300-308.

Honda, et al. 14-3-3 Zeta Protein Binds to the Carboxyl Half of Mouse Wee1Kinase. *Biochem. Biophys. Res. Commun.* 230: Jan. 1997. 262-265.

Tang, et al. Two Distinct Mechanisms for Negative Regulation of the Wee1 Protein Kinase. *EMBO J.* 12(9): Sep. 1993. 3427-3436.

* cited by examiner

*Primary Examiner*—Rebecca Prouty
(74) *Attorney, Agent, or Firm*—Thomas Fitting; Michael J. McCarthy

(57) ABSTRACT

The invention describes recombinant fusion proteins containing Wee1 protein sequences involved in checkpoint regulation of cell cycle, nucleic acid molecules that encode the fusion protein, and methods using the proteins for screening for compounds which modulate Wee1 or Cds1 function.

4 Claims, 5 Drawing Sheets

KINASE WEE1 FUSION PROTEIN COMPOSITIONS, NUCLEOTIDE SEQUENCES, EXPRESSION SYSTEMS, AND METHODS OF USE

This application is a division of U.S. patent application Ser. No. 09/646,075, filed Sep. 13, 2000, now U.S. Pat. No. 6,524,850, which is a 371 National Phase of PCT/US99/06704, filed Mar. 26, 1999, which claims the benefit of provisional application 60/079,752, filed Mar. 27, 1998.

This invention was made with government support under Contract No. CM 41281 by the National Institutes of Health. The government has certain rights in the invention.

TECHNICAL FIELD

The invention relates to methods and compositions for screening for compounds that inhibit or modulate phosphorylation of Wee1 fusion proteins by kinase Cds1.

BACKGROUND

Cell cycle checkpoints ensure that chromosomal DNA is replicated and repaired prior to nuclear division (Hartwell et al, *Science,* 246:629, 1989; L. Hartwell, *Cell,* 71:543, 1992; and S. J. Elledge, *Science,* 274:1664, 1996). In mammalian cells, loss of checkpoint control results in rearrangements, amplification, and loss of chromosomes, events that are causally associated with cancer. In yeasts, checkpoint controls are vital for survival when DNA is damaged or replication is inhibited.

Cdc2, the cyclin-dependent kinase that initiates mitosis, is the ultimate target of the DNA replication and repair checkpoints and is regulated by checkpoint kinases that couple mitosis to the completion of DNA replication and repair. The repair checkpoint kinase Chk1 regulates Cdc25, a phosphatase which activates Cdc2. In the fission yeast *Schizosaccharomyces pombe*, Cdc2 is inhibited by phosphorylation on tyrosine-15. This phosphorylation is catalyzed by the kinases Wee1 and Mik1 and reversed by the phosphatase Cdc25. Inhibitory phosphorylation of Cdc2 is crucial for replication and repair checkpoints in fission yeast and human cells (Enoch et al, *Cell,* 60:665, 1990; Lundgren et al, *Cell,* 64:1111, 1991; Jin et al, *J. Cell Biol.,* 134:963 (1996); Blasina et al, *Mol. Biol. Cell,* 8:1013, 1997; and Rhind et al, *Genes Dev.,* 11:504, 1997). Chk1 apparently enforces the DNA repair checkpoint by phosphorylating and inhibiting Cdc25 (Rhind et al, *Genes Dev.,* 11:504, 1997; Furnari et al, *Science,* 277:1495, 1997; Sanchez et al, *Science,* 277:1497 (1997); and Peng et al, *Science,* 277:1501, 1997). Chk1 is only required for the repair checkpoint, not the replication checkpoint evoked by hydroxyurea (HU)(Walworth et al, *Nature,* 363:368, 1993; and al-Khodairy et al, *Mol. Biol. Cell,* 5:147, 1994).

Thus, the kinase Wee1 participates in the regulation of cell cycle checkpoints during mitosis by catalyzing phosphorylation of the cyclin-dependent kinase that initiates mitosis, Cdc2. The role of Wee1 in these regulatory processes for controlling cell cycle are not well characterized.

The kinase Cds1 has also been implicated in the checkpoint process, although its role is not understood (Marukami et al, *Nature,* 374: 817, 1995).

There is a need for systems to characterize the role of Wee1 and Cds1 in regulation of cell cycle, and for screening for compounds which inhibit or modulate the effectors of these processes, particularly inhibitors of Wee1 or Cds1 function.

BRIEF SUMMARY OF THE INVENTION

It has now been discovered that Wee1 is phosphorylated by Cds1, and that Cds1 has an important role in the regulation of the replication checkpoint for mitosis. It has also been discovered that Wee1 can be used in various forms, including truncated proteins based on Wee1, in compositions and methods for evaluating the components of the Wee1-dependent processes related to replication checkpoint, particularly Cds1.

The invention therefore describes various nucleic acids which encode a truncated Wee1 protein, including expression vectors containing the nucleic acids for expressing the Wee1 protein. Also described are various forms of truncated Wee1 protein, particularly fusion proteins containing a Wee1 amino acid residue sequence which defines the functional site for phosphorylation by Cds1.

The invention describes methods for identifying compounds which modulate Wee1 function, or which modulate the ability of Cds1 to phosphorylate Wee1.

Other uses will be apparent to one skilled in the art in light of the present disclosures.

DESCRIPTION OF THE DRAWINGS

FIG. 1A is a photograph of a SDS-polyacrylamide gel analysis of GST:Wee1$^{152}$ and degradation products produced in bacteria and purified with GSH-Sepharose. The major degradation products are GST fused to ~70 aminoacids of Wee1 (GST:Wee1$^{70}$) and unfused GST. Proteins were stained with Coomassie Blue.

FIG. 1B is a photograph of an analysis of proteins from cells that were treated with 12 mM HU for a 1 hr time course at 30° C. Cell lysates were incubated with GST:Wee1 proteins bound to GSH-Sepharose. The GSH-Sepharose was washed and assayed for associated kinase activity. The positions of GST:Wee1$^{152}$ and GST:Wee1$^{70}$ following 12% SDS-polyacrylamide gel electrophoresis are shown.

FIG. 1C is a photograph of an analysis of proteins which illustrates that mutational inactivation of cdc22, encoding the large subunit of ribonucleotide reductase, enhances phosphorylation of GST:Wee1$^{70}$. Cells carrying the temperature sensitive cdc22-M45 allele or wild-type cells were grown at 25° C. The cultures were split and maintained at 25° C. or incubated at 35.5° C. for 90 min. GST:Wee1 phosphorylation assays were performed as described above.

FIG. 1D is a composite graph and photograph which illustrates activation of the kinase that phosphorylates GST:Wee1$^{70}$ in extracts from cdc25-22 cells released into HU from a G2 arrest. A culture of cdc25-22 cells grown at 25° C. was shifted to 35.5° C. for 4 hr. The culture was split and treated with 12 mM HU or mock-treated for 45 min at 35.5° C. Both cultures were returned to 25° C. and samples taken every 10 min. Septation index marks the completion of mitosis. Lysates from each time point were assayed for GST:Wee1$^{70}$ kinase. GST:Wee1$^{70}$ phosphorylation occurred in the HU-treated samples after exit from M, whereas phosphorylation of GST:Wee1$^{70}$ remained low in samples from the mock-treated culture. In the mock-treated culture, activity of the kinase that phosphorylates GST:Wee1$^{152}$ increased as cells underwent mitosis.

FIG. 2A is a photograph of an analysis of proteins which illustrates that phosphorylation of GST:Wee1[70] is dependent on Rad1 and Rad3. Wild-type, rad1 and rad3 strains cultures were split and treated for 1 hr with HU, or mock-treated, and then assayed for GST:Wee1[70] phosphorylation as described in FIG. 1.

FIG. 2B is a photograph of an analysis of proteins which illustrates that GST:Wee1[70] phosphorylation is dependent on Cds1 but not Chk1. Wild-type, chk1 and cds1 cultures were split and treated for 1 hr with HU or mock-treated. Phosphorylation of GST:Wee1 was assayed.

FIG. 2C is a photograph of an analysis of proteins which illustrates that Cds1 interacts with GST:Wee1 but not GST. Lysates from HU-treated cells expressing epitope tagged Cds1 (Cds1$^{HAHIS}$) expressed from the Cds1 genomic locus were incubated with GST or GST:Wee1 proteins bound to GSH-Sepharose. After extensive washing, samples were resolved by 10% SDS-polyacrylamide gel electrophoresis and subjected to immunoblotting with antibodies to HA and GST.

FIG. 2D is a photograph of an analysis of proteins which illustrates that Wee1 interacts with GST:cds1 but not GST:Chk1 in vivo. Strains carrying integrated nmt1:GST:chk1$^+$ or nmt1:GST:cds1$^+$ constructs were grown in minimal medium (EMM2) without thiamine at 30° C. for 16 hr to induce expression of GST fusion proteins. Cells were lysed and GST fusion proteins purified with GSH-Sepharose. After extensive washing, samples were resolved by 10% SDS-polyacrylamide gel electrophoresis and subjected to immunoblotting with antibodies to Wee1, Cdc25 and GST. A ~110 kDa protein corresponding to Wee1 was detected in the GST:Cds1 sample, whereas a ~80 kDa protein corresponding to Cdc25 was detected in the GST:Chk1 sample. The ~110 kDa protein was not detected in samples prepared from Δwee1 cells. GST:Cds1 and GST:Chk1 migrate at positions corresponding to ~82 and ~80 kDa, respectively.

FIG. 3A is a photograph of an analysis of proteins which illustrates that HU stimulates Cds1 binding to GST:Wee1[70]. A culture of cells expressing Cds1$^{HAHIS}$ from the cds1 genomic locus was split and treated for 3.5 hr with HU or mock-treated. The cultures were split again and samples processed for Ni$^{2+}$-NTA purification of Cds1$^{HAHIS}$ in denaturing conditions or purification of proteins that bind GST:Wee1 proteins in nondenaturing conditions. After extensive washing, samples were resolved by 10% SDS-polyacrylamide gel electrophoresis and subjected to immunoblot analysis.

FIG. 3B is a photograph of an analysis of proteins which illustrates that HU activates Cds1 kinase activity. In a separate experiment Cds1$^{HAHIS}$ was purified in native conditions and assayed for autophosphorylation activity (upper panel). Immunoblot analysis confirmed that similar amounts of Cds1$_{HAHIS}$ were recovered in the HU and mock-treated samples (lower panel).

FIG. 3C is a photograph of an analysis of proteins which illustrates that Cds1 and Rad3-dependent increase in Mik1 abundance in HU-treated cells. Wild-type, Cds1 and rad3 cells in which genomic mik1 encoded Mik1$^{HAHIS}$ protein were incubated for 4 hrs in YES at 25° C. with 12 mM HU or mock-treated. Mik1HARIS protein was purified by Ni$^{2+}$-NTA purification in denaturing conditions and detected by immunoblotting with antibodies to HA.

FIG. 3D is a photograph of cell cultures which illustrates that Mik1 is important for survival of HU treatment. Serial dilutions or wild-type and mik1 cells were plated in YES medium supplemented with 0 or 6 mM HU and incubated for 2 days at 30° C.

FIG. 5A shows that synchronous cultures were obtained by centrifugal elutriation. Progression through mitosis in the presence of 12 mM HU was monitored by scoring binucleate or septated cells. The cds1 chk1 double mutant and rad3 cells underwent mitosis in the presence of HU, whereas division was arrested in control strains (wild-type, Cds1 and chk1 single mutants).

FIG. 5B shows that the Cds1 chk1 double mutant and rad3 cells are equally hypersensitive to killing by 12 mM HU. Wild-type and chk1 cells were not sensitive to HU, whereas Cds1 cells were moderately sensitive.

DETAILED DESCRIPTION OF THE INVENTION

Figure 1:
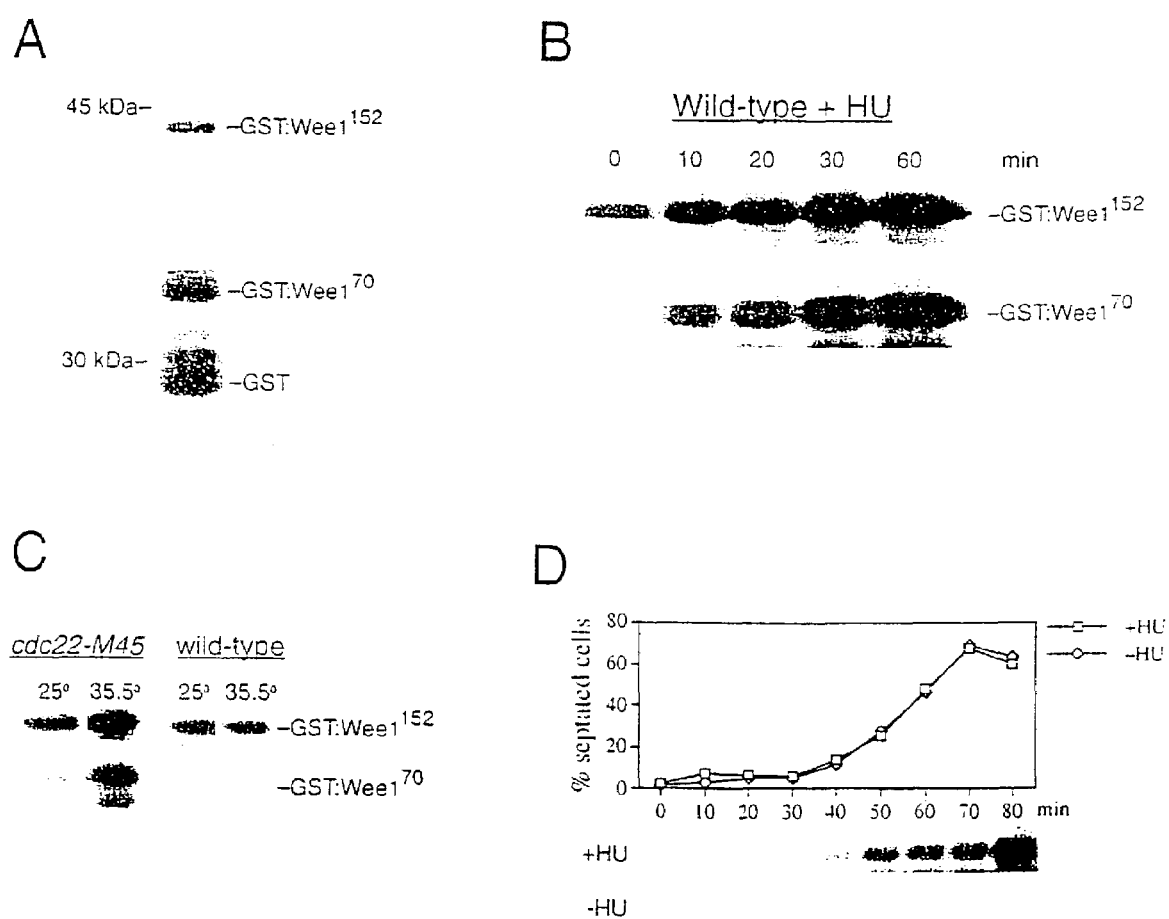
FIGS. 1A–1D illustrate the association of an HU-regulated kinase with the $NH_2$-terminus of Wee1 as described in Example 2.

The invention describes compositions and systems for screening for compounds which effect the role of Wee1 in cell cycle checkpoints. In particular, the invention describes a recombinant truncated protein containing Wee1 which can be used in combination with other components of the cell cycle, particularly Cds1, Chk1, Cdc2, Cdc25 and the like checkpoint proteins, in methods to identify and characterize regulatory pathways and to identify compounds which modulate and/or inhibit components in the pathways, particularly Cds1.

The invention describes particular fusion protein constructs, particularly GST:Wee1 fusion proteins, which are useful in the assays. The invention also describes an isolated nucleotide sequence which encodes truncated kinase Wee1 or a fusion protein containing truncated kinase Wee1. Also described are expression vectors for expression of a fusion protein of this invention.

In addition, the invention describes an assay for screening for modulators of check point regulation using Wee1 fusion proteins. A particular assay screens for compounds which modulate activity of kinase Wee1 or kinase Cds1.

A. Compositions

The invention describes compositions of truncated Wee1 proteins, isolated nucleic acids which encode the Wee1 proteins, expression vectors containing the nucleic acids useful for expressing a Wee1 protein of this invention. The Wee1 proteins are useful for evaluation Wee1 protein function, particularly for identifying modulators of Wee1 or Cds1 activity.

1. Truncated Wee1 Protein

In one embodiment, the invention describes a truncated Wee1 protein which is useful for evaluating Wee1 function and for screening for modulators of Wee1 or its effector molecule, Cds1. A truncated Wee1 protein of this invention is a polypeptide having an amino acid residue sequence derived from a native Wee1 protein, and which comprises the region of Wee1 which is a functional substrate of Cds1. Preferably, the truncated Wee1 protein has a sequence which substantially corresponds to the native Wee1 amino acid residue sequence, and more preferably has the same amino acid residue sequence as is found in native Wee1 protein.

By "substantially corresponds" means that there can be substitutions and/or deletions in the native Wee1 protein amino acid residue sequence so long as the biological activity of the Wee1 protein as a functional substrate of Cds1 is not substantially effected. That is, the truncated Wee1 protein with a modified sequence performs in the assays as described in the Examples for purposes of measuring Wee1 activity.

It is understood that the length of a Wee1 protein can vary so long as the region for performing as a functional Cds1 phosphorylation substrate is present, as described herein. A preferred truncated Wee1 protein comprises an amino acid residue sequence which corresponds to amino acid residues 11–70 of native Wee1, preferably residues 11–72 or 10–70 or 10–72. Particularly preferred is a protein that comprises residues 11–72. In a related embodiment, a truncated Wee1 protein comprises residues 11–152 or residues 10–152. Other combinations can also be easily be described and constructed by the methods described herein, and therefore, the invention should not be construed as so limited.

Wee1 is a large protein and the complete amino acid residue sequence and corresponding cDNA nucleotide sequence are well known and available on the Genbank database as accession number M16508.

By the term "truncated" is meant that the Wee1 protein is not the full length, wild-type Wee1 protein; instead a truncated protein contains amino acid residue deletions at either the amino or carboxy terminus of the wild-type sequence as described herein. Particularly preferred deletions include proteins in which residues 1–9, residues 1–10, residues 73–152 or residues 71–152 have been deleted.

Particularly preferred truncated Wee1 proteins are described in the Examples, and have an amino acid residue sequence shown in SEQ ID NO 1 for the GST:Wee1 (11–72) protein construct and shown in SEQ ID NO 3 for the GST:Wee1 (11–152) protein construct.

It is preferred that a subject truncated Wee1 protein be provided in the form of a fusion protein. That is, a protein which comprises a truncated Wee1 protein of the present invention operatively linked to a second protein where the operative linkage is in the form of a peptide bond typically found between amino acids of a polypeptide. Fusion proteins are well known in the art and are used because of the advantages provided by the presence of a second protein function provided by that second protein. These functions can include tags to facilitate isolation or identification of the fusion protein, to produce a bifunctional protein, and the like functions. In view of the state of the art relating to fusion proteins, the nature of the second protein is not considered to be the essential feature of the invention, and therefore is not to be construed as limiting. A preferred fusion protein includes glutathione-S-transferase (GST).

Exemplary fusion proteins, nucleotides, expression vectors and method for preparing the fusion proteins, nucleotides and vectors are described in the Examples.

2. Nucleic Acids and Expression Vectors

In another embodiment, the invention contemplates an isolated nucleic acid molecule which encodes a truncated Wee1 protein of this invention, and expression vectors capable of expressing the protein off of the nucleic acid.

A typical nucleic acid comprises a nucleotide sequence which, according to the genetic code, encodes a Wee1 protein of this invention, and therefore, the actual nucleotide sequence can vary depending upon the actual amino acid residue sequence and upon codon usage, as is well known.

A preferred nucleic acid encodes a protein comprising amino acid residues 11–70, and preferably comprises residues 10–70, residues 11–72, residues 11–152 or residues 10–152. A preferred nucleic acid encodes a fusion protein as described herein, preferably a GST:Wee1 fusion protein, and particularly a GST:Wee1(11–72) or GST:Wee1(11–152) protein.

Although not intended to be so limited, a preferred nucleic acid has a nucleotide sequence which encodes a Wee1 protein of this invention as shown in SEQ ID NO 2 or 4, or which encodes a GST:Wee1 fusion protein as shown in SEQ ID NO 2 or 4.

Also contemplated are expression vectors for expression of a truncated Wee1 protein of the present invention. An expression vector comprises a nucleic acid of the present invention operatively linked to the recombinant nucleic acid elements necessary for transcription and translation of the nucleic acid to express the encoded Wee1. Such transcription and translation expression control elements are well known in the art, and art not to be construed as limiting. These expression control elements can further include transcription enhancers, transcription promoters, translation initiators and terminators, and the like elements.

Preferred expression vectors are described in the Examples, or are commercially available from a variety of sources. Particularly preferred are the pGEX expression vectors commercially available. The complete nucleotide sequence of two preferred vectors are shown in SEQ ID NO 2 and 4, and correspond to pGEX-GST:Wee1(11–72) and pGEX-GST:Wee1(11–152), respectively.

B. Methods for Identifying Wee1 Modulators

The invention also contemplates a variety of methods for evaluating Wee1 function, and particularly for identifying modulators of Wee1 or modulators of Cds1, which phosphorylates Wee1. As shown by the examples, the analysis of the various components of the regulation of the cell cycle, particularly the replication checkpoint, can be carried out in a variety of formats, including by the use of isolated proteins, cell lysate containing one or more of the components, genetic strains of cells to provide different components of the checkpoint, all in combinations with the truncated Wee1 protein of this invention.

A preferred method involves the evaluation of the interaction between Cds1 and Wee1, where it is seen that Wee1 is a phosphorylation substrate for Cds1. The site in Wee1 for phosphorylation is in the amino terminal portion of the Wee1 protein designated as the functional Cds1 phosphorylation substrate as described herein.

Thus, in one embodiment, the invention describes a method for identifying a compound which modulates Cds1 kinase activity comprising the steps of:

a) combining:
   i) a test compound;
   ii) a truncated Wee1 protein of this invention, or a homolog thereof; and
   iii) a composition comprising Cds1 protein;

b) maintaining the combination of step (a) under conditions sufficient for Cds1 to phosphorylate said truncated Wee1 protein; and c) determining the amount of phosphorylated Wee1 protein whereby the amount of phosphorylated Wee1 indicates whether said test compound modulates the activity of Cds1.

In preferred embodiments, a truncated Wee1 protein comprises amino acid residues 11–70 of the native Wee1 protein as described herein, and preferably comprises amino acid residues 11–72, or 10–72 or 11–152 or 10–152 of native Wee1 protein.

In this method, the test compound can be any substance believed to have an effect on the ability of Cds1 to phosphorylate Wee1, and can include hydroxyurea (HU), components of the replication checkpoint pathway such as Cdc22, Cdc25, Chk1, Mik1, and the like components, genetic variants or mutants of these components of the checkpoint pathway, and any other molecule or test substance believed to be a drug candidate for modulating cell cycle checkpoints by inhibiting the phosphorylation interaction between Cds1 and Wee1.

The test reaction admixture further contains a truncated Wee1 protein according to the present invention, and can be provided in a variety of forms as described herein. The admixture further contains a composition comprising Cds1 protein which is capable of phosphorylating a truncated Wee1 protein of this invention in an amount sufficient to produce detectable phosphorylation under reaction conditions.

The source of Cds1 protein in a composition containing Cds1 protein can vary widely, and therefore the invention is not to be construed as so limited. For example, the protein can be in the form of an isolated protein provided in vitro to a reaction admixture. The Cds1 protein can be isolated by a variety of known methods including biochemical extraction or immuno-adsorption from cell lysates, expression of recombinant protein using cloned Cds1 cDNA, and the like methods known in the checkpoint kinase arts.

Cds1 protein can also be provided by preparing a lysate of a cell containing Cds1 protein as is described herein. Many different genetic strains of cells, such as yeast (e.g., *S. pombe*) stains, are available which express wild type (wt) or genetically variant Cds1 proteins suitable for use in the methods of the present invention, which strains and the preparation and handling of cell lysates are described in more detail in the Examples. In addition, as is shown herein, Cds1 binds to Wee1, and therefore can be isolated by use of the Sepharose bead isolation of GST:Wee1 protein following admixture with cell lysates containing Cds1, as described in the Examples.

The conditions for maintaining the combined admixture to allow Cds1 catalyzed phosphorylation of Wee1 are generally well known in the art, can vary widely depending upon the reaction format, and therefore are not to be considered as limiting. Examples of reaction conditions are described in the Examples and in the art, and include a variety of reaction components to support the biochemistry of phosphorylation of Wee1 by Cds1, including buffers, phosphate donors and the like.

Methods for determining amounts of a phosphorylation reaction can also vary widely, and depend in part on the nature of the reaction chemistry. Typically, the phosphate donor has a labeled phosphate leaving group, such as gamma-$P^{32}$, and the like labeled substrate. Detection can involve isolating the Wee1 protein and measuring the amount of label present on the Wee1 protein, such as is described in the Examples using SDS-gel electrophoresis and autography to measure the amount of radioactivity associated with the Wee1 protein.

Relative amounts of phosphorylation can be determined using comparisons to control reactions with known amounts of Cds1 protein, Wee1 protein and control reaction conditions, as is well known.

In a related embodiment, the invention contemplates a method for identifying a compound which modulates kinase Wee1 activity comprising the steps of:
  a) combining:
    i) a test compound;
    ii) a truncated Wee1 protein of this invention, or a homolog thereof; and
    iii) a reagent for Wee1;
  b) maintaining the combination of step (a) under conditions suitable for Wee1 to react with said reagent; and
  c) determining the amount Wee1 reacts with said reagent whereby the amount of reaction indicates whether said test compound modulates the activity of Wee1.

In preferred embodiments, a truncated Wee1 protein comprises amino acid residues 11–70 of the native Wee1 protein as described herein, and preferably comprises amino acid residues 11–72, or 10–72 or 11–152 or 10–152 of native Wee1 protein.

Many aspects of the above method are similar to the method described herein above for identifying modulators of Cds1 phosphorylation of Wee1, and therefore will not be discussed again.

In the method, a reagent for Wee1 refers to any compound or protein which interacts with Wee1 in a detectable reaction, and can include a cofactor for the reaction, a substrate for Wee1 kinase, or an enzyme which itself uses Wee1 as a substrate, any of which are modified in the reaction such that the amount of reaction can be measured.

Thus, for example, the reagent can be a phosphate donor substrate which reacts in the reaction admixture, such as a Cds1 kinase substrate that donates a labeled phosphate to Wee1 in the presence of Cds1 (e.g., [gamma-$P^{32}$]ATP). In this case, the determining comprises measuring phosphorylation of Wee1 protein. Alternatively, the reagent can be a Wee1 substrate such as Cdc22 which is phosphorylated by Wee1 as described herein, and the determining comprises measuring phosphorylation of Cdc22 similar to the procedures described herein.

Further exemplary method formats are described in the Examples.

EXAMPLES

The following examples illustrate, but do not limit, the present invention.

1. Preparation of GST:Wee1 Fusion Proteins

To study the role of Wee1 on Chk1, a model system was designed using fusion proteins based on Wee1. The rationale was developed because it was known that Chk1 is only required for the repair checkpoint, not the replication checkpoint evoked by hydroxyurea (HU)(Walworth et al, *Nature*, 363:368, 1993; and al-Khodairy et al, *Mol. Biol. Cell*, 5:147, 1994). However, an HU-induced arrest of cell cycle is rapidly abrogated after inactivation of temperature sensitive Wee1 protein in a mik1 background, showing that the replication checkpoint requires inhibitory phosphorylation of Cdc2. Wee1 and Mik1 are not individually required for an HU arrest, indicating that Wee1 and Mik1 may be coordinately regulated by the replication checkpoint. To test this hypothesis, a construct was made to evaluate whether Wee1 was phosphorylated by an HU-activated kinase, with attention focused on the $NH_2$-terminal regulatory domain (Aligue et al, *J. Biol. Chem.*, 272:13320, 1997).

To that end, a fusion of glutathione-S-transferase (GST) protein to amino-acids 10–152 of Wee1 was designed and constructed, and is designated GST:Wee1$^{52}$ (also referred to herein as GST:Wee1(11–152).

First, a PCR fragment was made encoding amino acids 10 to 152 of Wee1 using the known nucleotide sequence and amino acid residue sequence of the native Wee1 protein, incorporating a 5' NdeI site and 3' NotI site/stop codon into the fragment. This fragment was then cloned into a modified pGEX vector and transformed into the *E. coli* BL21 (DE3) expression host [Shiozaki et al, *Meth. Enz.*, 283:506 (1997)]. The expression vector construct is referred to herein as pGEX-GST:Wee1(11–152), and has a complete nucleotide sequence shown in SEQ ID NO 4.

Similarly, a fusion of GST protein to amino-acids 11–72 of Wee1 was designed and constructed, and is designated GST:Wee1$^{70}$ (also referred to herein as GST:Wee1(11–72). The expression vector construct is referred to herein as pGEX-GST:Wee1(11–72), and has a complete nucleotide sequence shown in SEQ ID NO 2.

Expression of a GST:Wee1 fusion protein by the pGEX expression vector in the BL21 host was induced by the addition of IPTG (1 mM) to exponentially growing cells at OD600=0.6 in LB media plus 50 μg/ml ampicillin at 37 C. After 2 hours at 37 C., cells were collected by centrifugation and stored at −70 C. in aliquots (200 μl pellet volume). Cells were lysed in 600 μl lysis buffer [50 mM Tris (pH 8), 150 mM NaCl, 5 mM EDTA, 10% glycerol, 0.1% NP-40, 5 μg/ml leupeptin/aprotinin/pepstatin, 1 mM PMSF] by sonication, centrifuged at 13,000×g for 10 min at 4 C. GSH-Sepharose (50 μl bead volume) was added to the supernatant and incubated at 4 C. for 30 min. The beads were then washed 3 times with 1 ml lysis buffer to yield expressed, isolated recombinant GST:Wee1 fusion protein.

The protein preparations yielded full-length GST:Wee1$^{1}$152 and GST:Wee1$^{70}$ (FIG. 1A), the latter being a truncation product containing ~70 amino acids of the amino terminal portion of Wee1 protein.

2. Evaluation of Wee1 Function in Cell-Cycle

The GST:Wee1$^{152}$ and GST:Wee1$^{70}$ proteins prepared in Example 1 were used to study yeast cellular functions. To that end, the isolated proteins were bound to glutathione (GSH)-Sepharose and mixed with cell lysates from the fission yeast *Schizosaccharomyces pombe* (*S. pombe*) harvested at intervals during incubation with hydroxyurea (HU).

The cell lysates were obtained from a variety of strains of *S. pombe* cells having the following genotypes: PR109, wild-type; NB2117, cds1::ura4+; NB2118, cds1:2HA6His:ura4+; NR1826, rad3::ura4+; OM591, cdc22-M45; NR1593, rad1::ura4+; NR1592,chk1::ura4+; BF1758, nmt1:GST:chk1:leu1+; BF1916, nmt1:GST:cds1:leu1+; OM2173, mik1:2HA6His:ura4+; OM2183, mik1:2HA6His:ura4+ cds1::ura4+; PR712, mik1::ura4+; and BF2115, cds1::ura4+ chk1::ura4+. All strains were leu1-32 ura4-D18. All nmt1 promoter constructs were integrated at the leu1-32 locus. Growth media and general methods for *S. pombe* have been described [Moreno et al, *Meth. Enzymol.*, 194:795 (1991)]. Unless otherwise indicated, yeast cultures were grown in YES medium at 30 C. YES consists of glucose, yeast extract and amino-acid supplements. Hydroxyurea was used at a concentration of 12 mM. Purification of GST fusion proteins and hexahis tagged proteins expressed in *S. pombe*, immunoblotting and kinase assays were performed as described [Shiozaki et al, *Nature*, 378:739 (1995)].

The proteins bound to GSH-Sepharose were washed, incubated with [gamma-$^{32}$P]ATP and analyzed by SDS-polyacrylamide gel electrophoresis (FIG. 1B). GST:Wee1$^{152}$ was phosphorylated in the 0 min sample, whereas GST:Wee1$^{70}$ phosphorylation was negligible. Phosphorylation of both proteins increased during incubation in HU. Unfused GST was not phosphorylated. Thus GST:Wee1$^{70}$ associates with and is phosphorylated by an HU-regulated kinase, whereas GST:Wee1$^{152}$ is phosphorylated by this kinase and another that is active prior to HU treatment.

Hydroxyurea prevents DNA replication by inhibiting ribonucleotide reductase and thereby reducing deoxyribonucleotide pools, but HU may also have other effects. However, mutational inactivation of cdc22, which encodes the large subunit of ribonucleotide reductase (Fernandez-Sarabia et al, *Mol. Gen. Genet.*, 238:241, 1993), caused phosphorylation of GST:Wee1$^{70}$ in cell lysates (FIG. 1C), indicating that the HU effect is due to inhibition of DNA replication.

GST:Wee1$^{70}$ phosphorylation was assayed in lysates from temperature sensitive cdc25-22 cells that were arrested in G2, incubated in HU for 45 min, and then released from G2 arrest in medium containing HU. Hydroxyurea failed to induce phosphorylation of GST:Wee1$^{70}$ in lysates prepared from cdc25-22 cells arrested in G2 (FIG. 1D). Upon release from G2, GST:Wee1$^{70}$ phosphorylation and cell septation increased coincidentally. Septation marks the end of mitosis (M) and the beginning of DNA replication (S), thus GST:Wee1$^{70}$ phosphorylation increased as cells encountered the HU arrest. No increase in GST:Wee1$^{70}$ phosphorylation was detected in a mock HU-treated culture (FIG. 1D). These observations indicate that the kinase that phosphorylates GST:Wee1$^{70}$ is activated when cells attempt DNA replication with insufficient deoxyribonucleotides.

Figure 2:
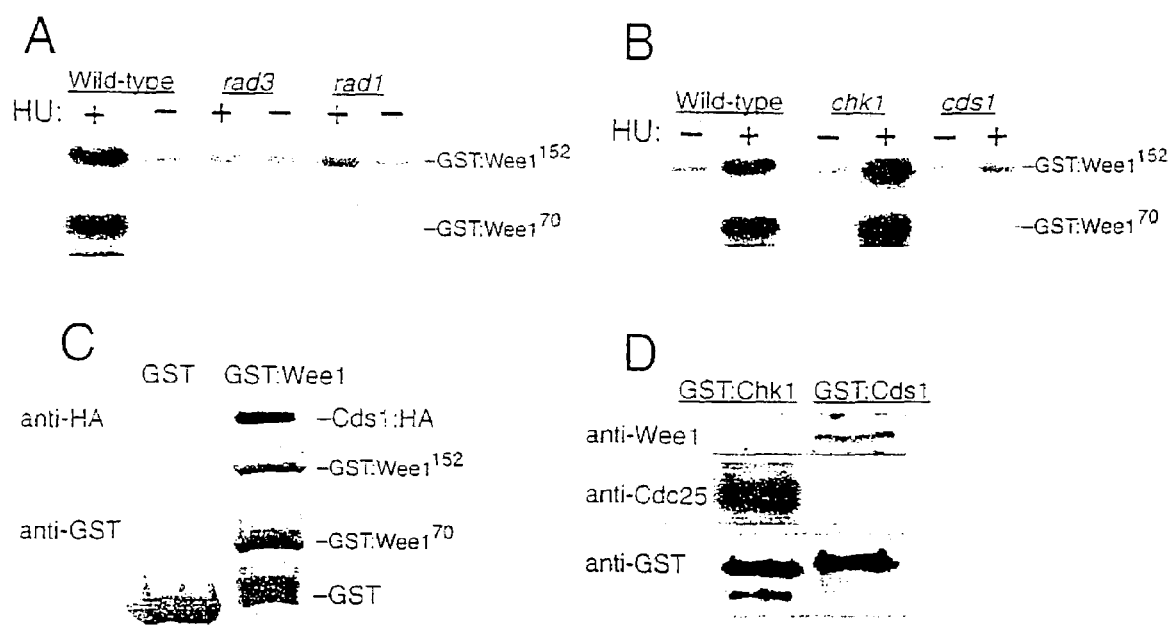
FIGS. 2A–2D illustrate that Cds1 is the kinase that phosphorylates GST:Wee1$^{70}$ as described in Example 2.

Phosphorylation of GST:Wee1$^{70}$ was abolished in lysates made from rad1 and rad3 checkpoint mutants (FIG. 2A), suggesting that the kinase which phosphorylates GST:Wee1$^{70}$ may be involved in the replication checkpoint. Experiments were undertaken to identify this kinase. Chk1 was excluded by experiments using lysates made from chk1 cells (FIG. 2B). The involvement of Cds1, a protein kinase that is important for survival of HU treatment (Murakami et al,

*Nature*, 374:817, 1995), was indicated by the observation that GST:Wee1$^{70}$ phosphorylation was abolished in a lysate prepared from HU-treated Cds1 cells (FIG. 2B). An experiment was performed to determine whether Cds1 co-precipitated with GST:Wee1$^{70}$. Lysates from HU-treated cells in which genomic Cds1 encoded a protein with a COOH-terminal HAHIS tag (consisting of two HA epitopes followed by hexahistidine) were incubated with GST:Wee1 or GST proteins, washed and analyzed by immunoblotting. Cds1$^{HAHIS}$ precipitated with GST:Wee1 but not unfused GST (FIG. 2C). Rad3 did not associate with GST:Wee1. Cds1 purified from fission yeast phosphorylated GST:Wee1$^{70}$ in vitro, producing a two-dimensional tryptic phosphopeptide map that was identical to a map made from GST™:Wee1$^{70}$ phosphorylated by its associated kinase. These data indicate that Cds1 is the HU-regulated kinase which associates with and phosphorylates GST:Wee1$^{70.}$ Association of Cds1 and Wee1 was also examined in vivo. GST:Cds1 was expressed from the thiamine-repressible nmt1 promoter.

To tag genomic cds1+ with a sequence encoding two copies of the HA epitope and hexahistidine, a PstI-NotI fragment having nucleotides 205-1465 of the cds1+ open reading frame was made by PCR. This was introduced into pRIP42-Spc1HA6H after digestion with PstI and NotI enzymes [Shiozaki et al, *Meth. Enz.*, 283:506 (1997)]. The construct was linearized with NheI and transformed into PR109. Integration and tagging was confirmed by Southern DNA hybridization and immunoblotting, with function of Cds1HAHIS confirmed by lack of HU sensitivity. The nmt1:GST:cds1+ construct was prepared as described for the nmt1:GST:chk1+ construct (Furnari et al, *Science*, 277: 1495, 1997).

As a control, a strain that expressed GST:Chk1 was used. The GST fusion proteins were purified with GSH-Sepharose and analyzed by immunoblotting. Cdc25 (but not Wee1) associated with GST:Chk1, whereas Wee1 (but not Cdc25) associated with GST:Cds1 (FIG. 2D).

Figure 3:
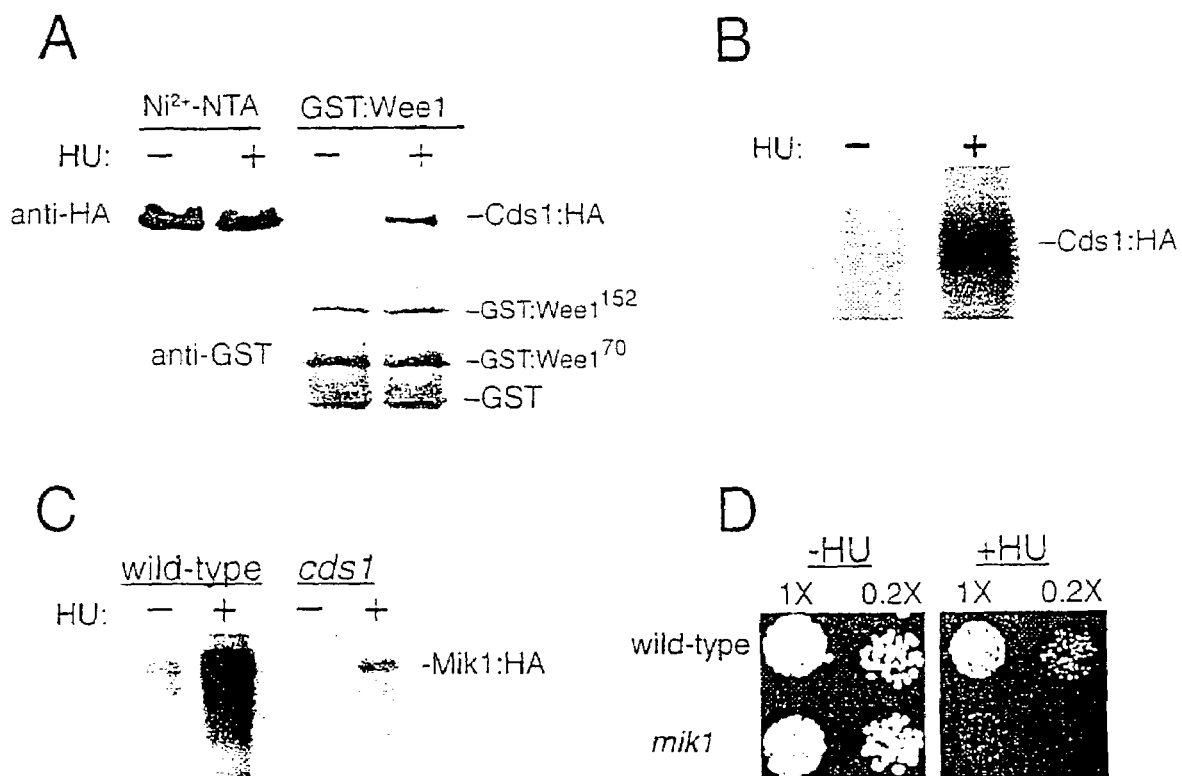
FIGS. 3A–3D illustrate that HU stimulates Cds1 kinase activity, binding of Cds1 to GST:Wee1[70] in lysates and accumulation of Mik1 as described in Example 2.

HU may increase the abundance of Cds1, or it may make Cds1 competent to associate with Wee1, or perhaps the replication checkpoint enhances the kinase activity of Cds1. Cells expressing Cds1$^{HAHIS}$ were treated with HU or mock-treated; lysates were made and precipitated with GST:Wee1 proteins. Association of Cds1$^{HAHIS}$ with GST:Wee1 was detected in lysates from cells treated with HU, whereas no Cds1$^{HAHIS}$ associated with GST:Wee1 in mock-treated samples (FIG. 3A). Ni$^{2+}$-NTA precipitation of Cds1$^{HAHIS}$ via the hexahistidine sequence showed that Cds1$^{HAHIS}$ was equally abundant in HU-treated and mock-treated cell lysates. Therefore, HU-treatment enhanced association of Cds1 with GST:Wee1. The in vivo interaction between GST:Cds1 and Wee1 shown in FIG. 2D did not require HU treatment, presumably because GST:Cds1 was over expressed.

Cds1$^{HAHIS}$ was also purified from HU or mock-treated cells and assayed in an autophosphorylation assay. Phosphorylation of Cds1 was increased in samples from cells treated HU (FIG. 3B). Similar results were obtained using GST:Wee1$_{70}$ as a substrate. Thus HU apparently both activates Cds1 as a kinase and stimulates binding to Wee1.

Phosphorylation of Wee1 by Cds1 may play a role in the DNA replication checkpoint. However, wee1 mutants arrest division in response to HU (Enoch et al, *Cell*, 60:665, 1990), thus another protein that controls Cdc2 Tyr$^{15}$ phosphorylation must also be regulated by the replication checkpoint. The kinase Mik1 phosphorylates Cdc2 on Tyr$^{15}$ (Lundgren et al, *Cell*, 64:1111, 1991), therefore the abundance of Mik1 was monitored in HU-treated cells using a strain expressing Mik1$^{HAHIS}$ from the genomic locus. Immunoblot analysis showed that the amount of Mik1$^{HAHIS}$ increased in cells treated with HU (FIG. 3C). The abundance of mik1 mRNA was unchanged in HU-treated cells, thus HU must influence Mik1$_{HAHIS}$ synthesis or turnover. The HU-induced increase of Mik1$^{HAHIS}$ was largely abolished in cds1 and rad3 cells (FIG. 3C), indicating that this response was regulated by the replication checkpoint. Mik1 is a dose-dependent inhibitor of mitosis (Lundgren et al, *Cell*, 64:1111, 1991), thus the increase of Mik1 abundance in HU-treated cells should help to enforce the checkpoint. Indeed, mik1 mutants exhibited enhanced sensitivity to HU (FIG. 3D).

Figure 4:
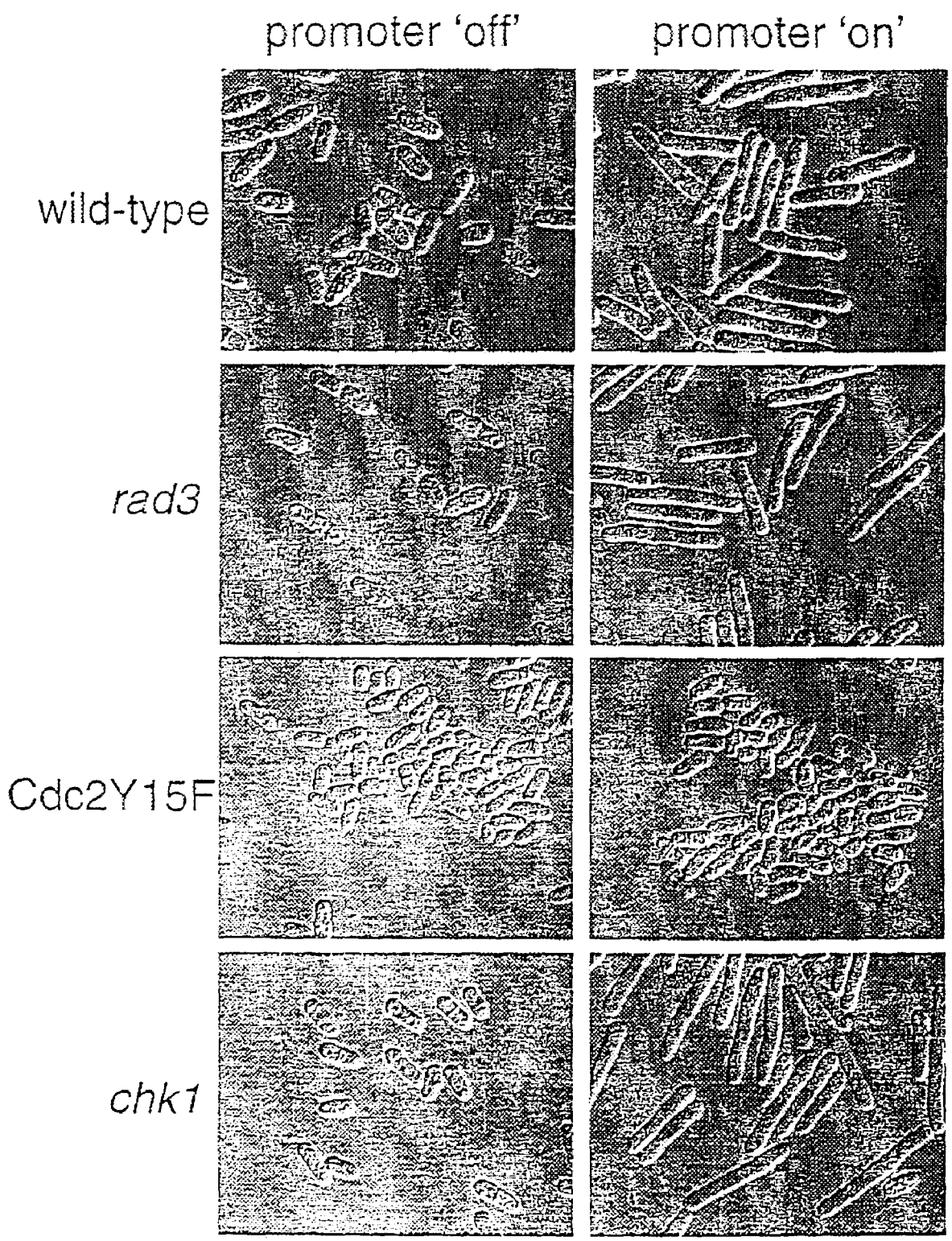
FIG. 4 illustrates that Cell cycle arrest caused by expression of large amounts of GST:Cds1 as described in Example 2. Cells having an integrated nmt1:GST:cds1$^+$ construct were incubated in nmt1-repressing medium (promoter "off") or inducing medium (promoter "on") for 19 hrs at 30° C. GST:Cds1 expression induced cell cycle arrest in wild-type, rad3 and chk1 strains. Flow cytometry analysis confirmed that these cells were arrested with a 2C DNA content. Cells expressing Cdc2Y15F, a form of Cdc2 in which tyrosine at position 15 is replaced with phenylalanine, were insensitive to GST:Cds1.

Expression of a large amount of GST:Cds1 from the nmt1 promoter caused a cell cycle arrest, as indicated by highly elongated cells (FIG. 4). The arrest occurred in rad3 and chk1 mutants, indicating that Cds1 functions downstream of Rad3 and independently of Chk1. Expression of GST:Cds1 had no effect in cells that express Cdc2Y15F, a form of Cdc2 that cannot be phosphorylated by Wee1 or Mik1. These findings support the conclusion that Cds1 transmits a checkpoint signal.

Cells lacking Cds1 arrest division in response to HU, indicating that the Cds1 signal is supplemented by other checkpoint proteins (Murakami et al, *Nature*, 374:817, 1995). The replication checkpoint was examined in synchronous cultures of Cds1 chk1 double mutant cells, cds1, chk1, rad3 single mutants or wild-type cells.

Cells were first grown in YES (yeast extract and glucose) medium to an OD600 of 1.0 and then treated with HU (12 mM) for 90 min at 30 C. Synchronous cells were then obtained by centrifugal elutriation with a Beckman JE-5.0 elutriation rotor. These cells were diluted to an OD600 of 0.3 in YES containing 12 mM HU and grown at 30 C. for a further 4 hr. Cells were scored for progression through mitosis by microscopic observation. HU sensitivity studies were carried out with cells grown to an OD600 of 0.3 in YES medium and then diluted to 13,000 cells/ml in YES media containing HU (12 mM), followed by growth at 30 C. for a further 8 hr. Samples (75 µl) were taken at regular intervals, plated onto YES plates and grown for 4 days at 30 C. to determine survival.

Figure 5:
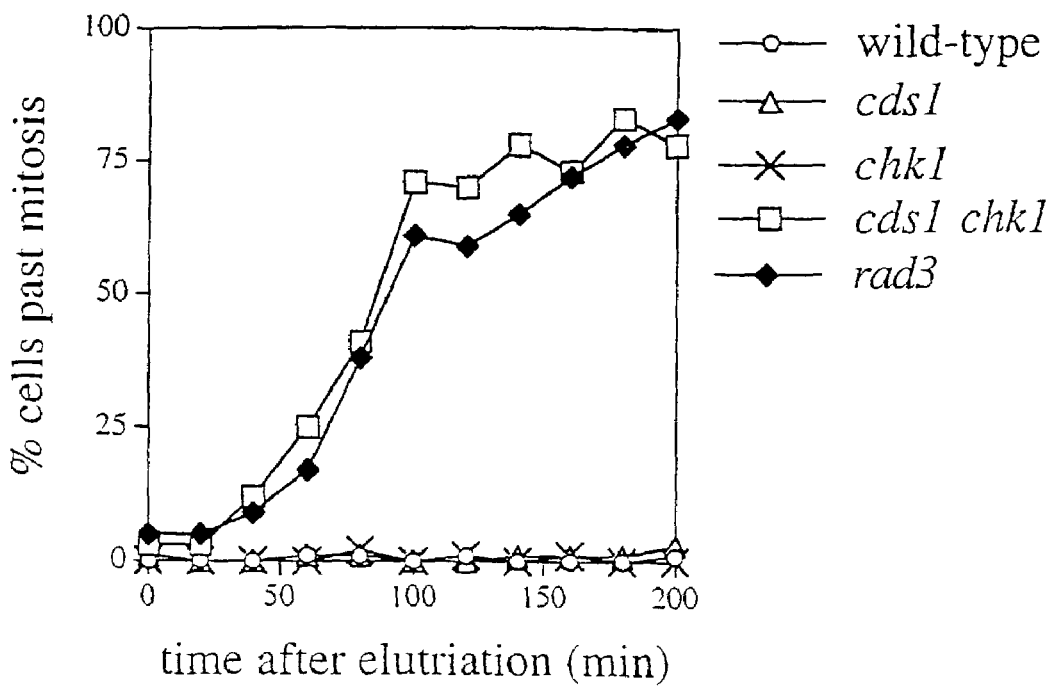
FIGS. 5A–5B are graphs which illustrate that replication checkpoint is abolished in Cds1 chk1 cells as described in Example 2.
Figure 5:
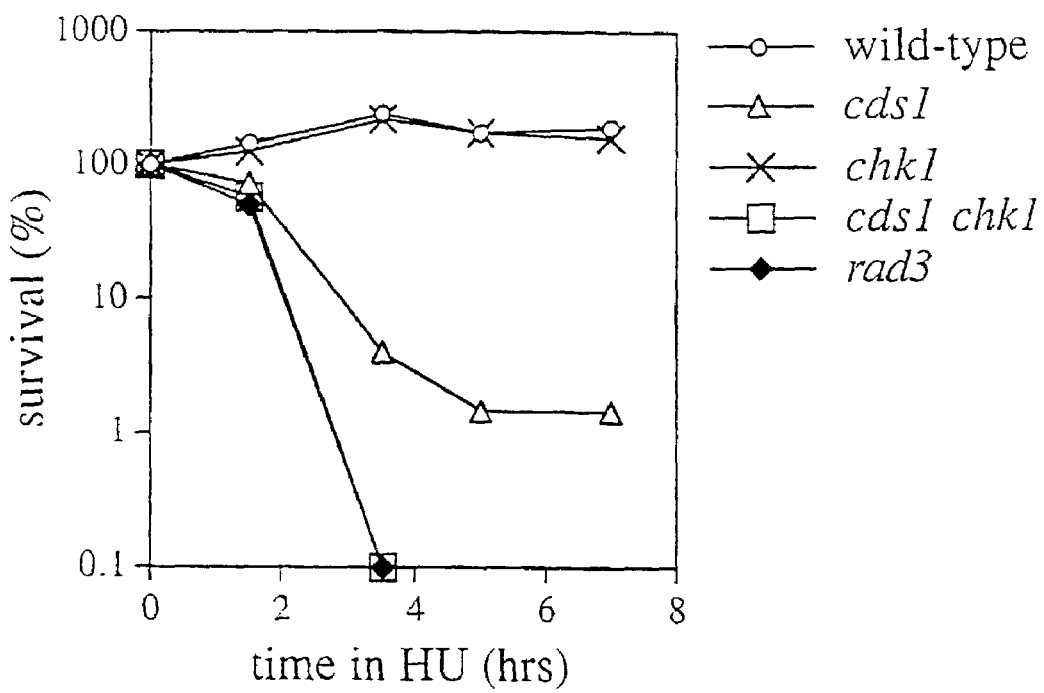

HU arrested division in wild-type cells, Cds1 and chk1 single mutants (FIG. 5A). In contrast, Cds1 chk1 double mutant cells underwent division with kinetics that were similar to rad3 cells. Thus the checkpoint is abolished in Cds1 chk1 cells. Indeed, the Cds1 chk1 double mutant cells were acutely sensitive to killing by HU (FIG. 5B). These findings are consistent with a recent study (Lindsay et al, *Genes Dev.*, 12:382, 1998) and support a model in which Cds1 has a direct role in enforcing the replication checkpoint.

These findings indicate that Cds1 and Chk1 are dual effectors of the replication checkpoint. Chk1 regulates Cdc25, whereas Cds1 appears to phosphorylate Wee1 and is required to increase the abundance of Mik1. The effect of phosphorylation of Wee1 by Cds1 is unknown and remains to be confirmed with in vivo studies, but it is striking that the replication checkpoint both increases the kinase activity of Cds1 and stimulates binding to Wee1 in cell extracts. The large HU-induced increase in the abundance of Mik1 helps to explain why cdc25 wee1 double mutant cells arrest division in response to HU and reaffirms the importance of Cdc2 Tyr$^{15}$ phosphorylation in the replication checkpoint (Enoch et al, *Genes Dev.*, 6:2035, 1993). Cds1 shares significant sequence identity with the kinase Rad53p, a protein involved in the DNA replication checkpoint in *Saccharomyces cerevisiae* (S. J. Elledge, *Science*, 274:1664, 1996).

Effectors of the replication checkpoint evoked by hydroxyurea (HU) were previously unknown. Treatment of fission yeast with HU stimulated the kinase Cds1 which phosphorylates the kinase Wee1, an inhibitor of Cdc2. The protein kinase Cds1 was also required for a large HU-induced increase in the amount of Mik1, a second inhibitor of Cdc2. HU-induced arrest of cell division was abolished in cds1 chk1 cells. Thus Cds1 and Chk1 jointly enforce the replication checkpoint.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for identifying a compound which modulates kinase Wee1 activity comprising the steps of:
   a) combining:
      i) a test compound;
      ii) a glutathione-Stransferase (GST):Wee1 fusion protein comprising the amino acid residue sequence in SEQ ID NO: 1; and
      iii) a reagent for Wee1
   b) maintaining the combination of step (a) under conditions suitable for Wee1 to react with said reagent; and
   c) determining the amount of phosphorylation of said Wee1 fusion protein in the presence of the test compound and in the absence of the test compound, whereby a difference in the amount of reaction phosphorylation in the presence of the test compound and in the absence of the test compound indicates that said test compound modulates the activity of Wee1.

2. The method of claim 1 wherein said test compound is hydroxyurea.

3. The method of claim 1 wherein said test compound is a test protein selected from the group consisting of Cdc22, Cdc25, Cds1, Chk1, Mik1, and genetic variants thereof.

4. The method of claim 1 wherein said glutathione-S-transferase (GST):Wee1 fusion protein comprises the amino acid residue sequence in SEQ ID NO: 3.

* * * * *

SEQUENCE LISTING

```
<160> NUMBER OF SEQ ID NOS: 4
<210> SEQ ID NO 1
<211> LENGTH: 310
<212> TYPE: PRT
<213> ORGANISM: Artificial Sequence
<220> FEATURE:
<223> OTHER INFORMATION: Description of Artificial Sequence:  Synthetic
      fusion protein GST:Wee1 (11-72).

<400> SEQUENCE: 1

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Gly Ile Ser Gly Gly Gly Gly Ile His Met Arg Ser
225                 230                 235                 240

Tyr Gly Leu Arg Arg Ser Gln Arg Ser Met Asn Leu Asn Arg Ala Thr
                245                 250                 255

Leu Leu Ala Pro Pro Thr Pro Ser Ser Leu Tyr Asp Ala Asn Asn Ser
            260                 265                 270

Thr Ser Ser Thr Ser Ser Gln Lys Pro Asn Thr Ser Phe Thr Ser Leu
        275                 280                 285

Phe Gly Pro Arg Lys Gln Thr Thr Ser Ser Pro Ser Phe Ser His Ala
    290                 295                 300

Ala Pro Leu His Pro Leu
305                 310

<210> SEQ ID NO 2
<211> LENGTH: 3175
<212> TYPE: DNA
<213> ORGANISM: Artificial Sequence
```

<220> FEATURE:
<223> OTHER INFORMATION: Description of Artificial Sequence: Synthetic
nucleotide sequence encoding fusion protein
GST:Wee1 (11-72).

<400> SEQUENCE: 2

```
gcggccgctc aggtggcact tttcggggaa atgtgcgcgg aaccccctatt tgtttatttt      60 tctaaataca ttcaaatatg tatccgctca tgagacaata ccctgataa atgcttcaat      120 aatattgaaa aggaagagt atgagtattc aacatttccg tgtcgccctt attcccttt       180 ttgcggcatt ttgccttcct gttttttgctc acccagaaac gctggtgaaa gtaaaagatg      240
ctgaagatca gttgggtgca cgagtgggtt acatcgaact ggatctcaac agcggtaaga     300
tccttgagag ttttcgcccc gaagaacgtt ttccaatgat gagcactttt aaagttctgc     360
tatgtggcgc ggtattatcc cgtattgacg ccgggcaaga gcaactcggt cgccgcatac     420
actattctca gaatgacttg gttgagtact caccagtcac agaaaagcat cttacggatg     480
gcatgacagt aagagaatta tgcagtgctg ccataaccat gagtgataac actgcggcca     540
acttacttct gacaacgatc ggaggaccga aggagctaac cgcttttttg cacaacatgg     600
gggatcatgt aactcgcctt gatcgttggg aaccggagct gaatgaagcc ataccaaacg     660
acgagcgtga caccacgatg cctgtagcaa tggcaacaac gttgcgcaaa ctattaactg     720
gcgaactact tactctagct tcccggcaac aattaataga ctggatggag gcggataaag     780
ttgcaggacc acttctgcgc tcggcccttc cggctggctg gtttattgct gataaatctg     840
gagccggtga gcgtgggtct cgcggtatca ttgcagcact ggggccagat ggtaagccct     900
cccgtatcgt agttatctac acgacgggga gtcaggcaac tatggatgaa cgaaatagac     960
agatcgctga gataggtgcc tcactgatta agcattggta actgtcagac caagtttact     1020
catatatact ttagattgat ttaaaacttc atttttaatt taaaaggatc taggtgaaga    1080
tcctttttga taatctcatg accaaaatcc cttaacgtga gttttcgttc cactgagcgt    1140 cagacccccgt agaaaagatc aaaggatctt cttgagatcc ttttttttctg cgcgtaatct    1200 gctgcttgca acaaaaaaaa ccaccgctac cagcggtggt ttgtttgccg gatcaagagc    1260
taccaactct ttttccgaag gtaactggct tcagcagagc cagataccaa atactgtcc     1320 ttctagtgta gccgtagtta ggccaccact tcaagaactc tgtagcaccg cctacatacc    1380
tcgctctgct aatcctgtta ccagtggctg ctgccagtgg cgataagtcg tgtcttaccg    1440
ggttggactc aagacgatag ttaccggata aggcgcagcg tcgggctga acggggggtt     1500 cgtgcacaca gcccagcttg gagcgaacga cctacaccga actgagatac ctacagcgtg    1560
agcattgaga aagcgccacg cttcccgaag ggagaaaggc ggacaggtat ccggtaagcg    1620
gcagggtcgg aacaggagag cgcacgaggg agcttccagg gggaaacgcc tggtatctt     1680 atagtcctgt cgggtttcgc cacctctgac ttgagcgtcg attttttgtga tgctcgtcag    1740 gggggcggag cctatggaaa aacgccagca acgcggcctt tttacggttc ctggccttt      1800 gctggccttt tgctcacatg ttctttcctg cgttatcccc tgattctgtg ataaccgta     1860 ttaccgcctt tgagtgagct gataccgctc gccgcagccg aacgaccgag cgcagcgagt    1920
cagtgagcga ggaagcggaa gagcgcccaa tacgcaaacc gcctctcccc gcgcgttggc    1980
cgattcatta atgcagcctc gaggtctgca ccaatgcttc tggcgtcagg cagccatcgg    2040
aagctgtggt atggctgtgc aggtcgtaaa tcactgcata attcgtgtcg ctcaaggcgc    2100
actcccgttc tggataatgt tttttgcgcc gacatcataa cggttctggc aaatattctg    2160
```

-continued

```
aaatgagctg ttgacaatta atcatcggct cgtataatgt gtggaattgt gagcggataa    2220
caatttcaca caggaaacag tattcatgtc ccctatacta ggttattgga aaattaaggg    2280
ccttgtgcaa cccactcgac ttctttttgga atatcttgaa gaaaaatatg aagagcattt   2340
gtatgagcgc gatgaaggtg ataaatggcg aaacaaaaag tttgaattgg gtttggagtt    2400
tcccaatctt ccttattata ttgatggtga tgttaaatta acacagtcta tggccatcat    2460
acgttatata gctgacaagc acaacatgtt gggtggttgt ccaaaagagc gtgcagagat    2520
ttcaatgctt gaaggagcgg ttttggatat tagatacggt gtttcgagaa ttgcatatag    2580
taaagacttt gaaactctca aagttgattt tcttagcaag ctacctgaaa tgctgaaaat    2640
gttcgaagat cgtttatgtc ataaaacata tttaaatggt gatcatgtaa cccatcctga    2700
cttcatgttg tatgacgctc ttgatgttgt tttatacatg gacccaatgt gcctggatgc    2760
gttcccaaaa ttagtttgtt ttaaaaaacg tattgaagct atcccacaaa ttgataagta    2820
cttgaaatcc agcaagtata tagcatggcc tttgcagggc tggcaagcca cgtttggtgg    2880
tggcgaccat cctccaaaat cggatctggt tccgcgtgga tccccgggaa tttccggtgg    2940
tggtggtgga attcatatga gatcttatgg cttacggcgg tcccaacgct ccatgaatct    3000
aaatcgtgct actttgctcg ctcctccaac tccatcgagc ctgtatgatg ctaacaattc    3060
tacttcatct acctcttcgc aaaagccaaa tacctctttc actagcttat tcggtcctcg    3120
caaacagacc acttcctccc cttccttctc tcatgccgcc cctcttcacc ctctt          3175
```

<210> SEQ ID NO 3
<211> LENGTH: 379
<212> TYPE: PRT
<213> ORGANISM: Artificial Sequence
<220> FEATURE:
<223> OTHER INFORMATION: Description of Artificial Sequence: Synthetic
      fusion protein GST:Wee1 (11-152).

<400> SEQUENCE: 3

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
```

```
                       180               185               190
Leu Lys Ser Ser Lys Tyr Ile Ala Trp Pro Leu Gln Gly Trp Gln Ala
            195                 200                 205
Thr Phe Gly Gly Gly Asp His Pro Pro Lys Ser Asp Leu Val Pro Arg
    210                 215                 220
Gly Ser Pro Gly Ile Ser Gly Gly Gly Gly Ile His Met Arg Ser
225                 230                 235                 240
Tyr Gly Leu Arg Arg Ser Gln Arg Ser Met Asn Leu Asn Arg Ala Thr
                245                 250                 255
Leu Leu Ala Pro Pro Thr Pro Ser Ser Leu Tyr Asp Ala Asn Asn Ser
            260                 265                 270
Thr Ser Ser Thr Ser Ser Gln Lys Pro Asn Thr Ser Phe Thr Ser Leu
        275                 280                 285
Phe Gly Pro Arg Lys Gln Thr Thr Ser Ser Pro Ser Phe Ser His Ala
    290                 295                 300
Ala Pro Leu His Pro Leu Ser Pro Pro Ser Phe Thr His Ser Gln Pro
305                 310                 315                 320
Gln Ile Gln Ala Gln Pro Val Pro Arg Arg Pro Ser Leu Phe Asp Arg
                325                 330                 335
Pro Asn Leu Val Ser Arg Ser Ser Arg Leu Gly Asp Ser Pro Ser
            340                 345                 350
Leu Ser Pro Val Ala Gln Val Ala Asn Pro Ile His His Thr Ala Pro
        355                 360                 365
Ser Pro Ser Asp Val Arg Ala Phe Pro Ile His
    370                 375

<210> SEQ ID NO 4
<211> LENGTH: 3867
<212> TYPE: DNA
<213> ORGANISM: Artificial Sequence
<220> FEATURE:
<223> OTHER INFORMATION: Description of Artificial Sequence:  Synthetic
      nucleotide sequence encoding fusion protein
      GST:Wee1 (11-152).

<400> SEQUENCE: 4
gcggccgctc aggtggcact tttcggggaa atgtgcgcgg aaccccctatt tgtttatttt      60 tctaaataca ttcaaatatg tatccgctca tgagacaata accctgataa atgcttcaat     120
aatattgaaa aaggaagagt atgagtattc aacatttccg tgtcgccctt attccctttt     180
ttgcggcatt ttgccttcct gttttttgctc acccagaaac gctggtgaaa gtaaaagatg     240
ctgaagatca gttgggtgca cgagtgggtt acatcgaact ggatctcaac agcggtaaga     300
tccttgagag ttttcgcccc gaagaacgtt ttccaatgat gagcactttt aaagttctgc     360
tatgtggcgc ggtattatcc cgtattgacg ccgggcaaga gcaactcggt cgccgcatac     420
actattctca gaatgacttg gttgagtact caccagtcac agaaaagcat cttacggatg     480
gcatgacagt aagagaatta tgcagtgctg ccataaccat gagtgataac actgcggcca     540
acttacttct gacaacgatc ggaggaccga aggagctaac cgcttttttg cacaacatgg     600
gggatcatgt aactcgcctt gatcgttggg aaccggagct gaatgaagcc ataccaaacg     660
acgagcgtga ccacgatg cctgtagcaa tggcaacaac gttgcgcaaa ctattaactg     720
gcgaactact tactctagct tcccggcaac aattaataga ctggatggag gcggataaag     780
ttgcaggacc acttctgcgc tcggcccttc cggctggctg gtttattgct gataaatctg     840
gagccggtga gcgtgggtct cgcggtatca ttgcagcact ggggccagat ggtaagccct     900
```

```
cccgtatcgt agttatctac acgacgggga gtcaggcaac tatggatgaa cgaaatagac     960
agatcgctga gataggtgcc tcactgatta agcattggta actgtcagac caagtttact    1020
catatatact ttagattgat ttaaaacttc attttttaatt taaaaggatc taggtgaaga    1080
tcctttttga taatctcatg accaaaatcc cttaacgtga gttttcgttc cactgagcgt    1140
cagaccccgt agaaaagatc aaaggatctt cttgagatcc ttttttttctg cgcgtaatct   1200
gctgcttgca acaaaaaaa ccaccgctac cagcggtggt ttgtttgccg gatcaagagc     1260
taccaactct ttttccgaag gtaactggct tcagcagagc gcagatacca atactgtcc     1320
ttctagtgta gccgtagtta ggccaccact tcaagaactc tgtagcaccg cctacatacc    1380
tcgctctgct aatcctgtta ccagtggctg ctgccagtgg cgataagtcg tgtcttaccg    1440
ggttggactc aagacgatag ttaccggata aggcgcagcg gtcgggctga acggggggtt    1500
cgtgcacaca gcccagcttg gagcgaacga cctacaccga actgagatac ctacagcgtg    1560
agcattgaga aagcgccacg cttcccgaag ggagaaaggc ggacaggtat ccggtaagcg    1620
gcagggtcgg aacaggagag cgcacgaggg agcttccagg gggaaacgcc tggtatcttt    1680
atagtcctgt cgggtttcgc cacctctgac ttgagcgtcg attttttgtga tgctcgtcag   1740
gggggcggag cctatggaaa aacgccagca acgcggcctt tttacggttc ctggcctttt    1800
gctggccttt tgctcacatg ttctttcctg cgttatcccc tgattctgtg gataaccgta    1860
ttaccgcctt tgagtgagct gataccgctc gccgcagccg aacgaccgag cgcagcgagt    1920
cagtgagcga ggaagcggaa gagcgcccaa tacgcaaacc gcctctcccc gcgcgttggc    1980
cgattcatta atgcagcctc gaggtctgca ccaatgcttc tggcgtcagg cagccatcgg    2040
aagctgtggt atggctgtgc aggtcgtaaa tcactgcata attcgtgtcg ctcaaggcgc    2100
actcccgttc tggataatgt ttttttgcgcc gacatcataa cggttctggc aaatattctg   2160
aaatgagctg ttgacaatta atcatcggct cgtataatgt gtggaattgt gagcggataa    2220
caatttcaca caggaaacag tattcatgtc ccctatacta ggttattgga aaattaaggg    2280
ccttgtgcaa cccactcgac ttcttttgga atatcttgaa gaaaaatatg aagagcattt    2340
gtatgagcgc gatgaaggtg ataaatggcg aaacaaaaag tttgaattgg gtttggagtt    2400
tcccaatctt ccttattata ttgatggtga tgttaaatta acacagtcta tggccatcat    2460
acgttatata gctgacaagc acaacatgtt gggtggttgt ccaaaagagc gtgcagagat    2520
ttcaatgctt gaaggagcgg ttttggatat tagatacggt gtttcgagaa ttgcatatag    2580
taaagacttt gaaactctca agttgatttt cttagcaag ctacctgaaa tgctgaaaat     2640
gttcgaagat cgtttatgtc ataaaacata tttaaatggt gatcatgtaa cccatcctga    2700
cttcatgttg tatgacgctc ttgatgttgt tttatacatg gacccaatgt gcctggatgc    2760
gttcccaaaa ttagtttgtt ttaaaaaacg tattgaagct atcccacaaa ttgataagta    2820
cttgaaatcc agcaagtata tagcatggcc tttgcagggc tggcaagcca cgtttggtgg    2880
tggcgaccat cctccaaaat cggatctggt tccgcgtgga tccccgggaa tttccggtgg    2940
tggtggtgga attcatatga gatcttatgg cttacggcgg tcccaacgct ccatgaatct    3000
aaatcgtgct actttgctcg ctcctccaac tccatcgagc ctgtatgatg ctaacaattc    3060
tacttcatct acctcttcgc aaaagccaaa tacctctttc actagcttat tcggtcctcg    3120
caaacagacc acttcctccc cttccttctc tcatgccgcc cctcttcacc ctctttctcc    3180
tccttctttt acacattcac aaccccagat acaggcacaa cctgtacctc ggcggccttc    3240
```

```
cctttttgat agacccaatc tggtatcacg ctcttcctct cggttaggtg attctccatc    3300
tctttctcct gttgcccagg tggctaatcc catccaccat actgcccctt caccctcaga    3360
cgttcgtgcg tttcccattc attaagcggc gcaagcttaa attggccctg caggcctgga    3420
aggcatcctc ctccatgatt gtgggcaccc aggagcccag gctgctgtga gctgggtctg    3480
ggacacttgg ccagagggga ttcttcctgt tggggctgca acagagccag gcagttccac    3540
agaggcaggt gagcaacagc aggaggccga acaggcccag gatgatgtgt agctccgacc    3600
cctctggggt caaggtcatc agggtgagga ctgtactgtt ggtggcccca gcctggctgg    3660
cagccatgag gtggatgtga tacagactgg cgggctccag gccatggagg acaaagccac    3720
gggaggaggc attcaggatg gcggagaagg actggttctg agcgttggtc cagaagatgg    3780
tgtagtgggt aaggggctc ttccccagct caggggctc aggcacccac tccaggcctg    3840
cagggccaat tctagatgac taagctt                                        3867
```